United States Patent [19]

Wynkoop et al.

[11] 4,093,528
[45] June 6, 1978

[54] TEREPHTHALIC ACID PROCESS

[75] Inventors: Raymond Wynkoop, Media, Pa.;
Oscar L. Norman; Richard V. Norton, both of Wilmington, Del.

[73] Assignee: Suntech, Inc., Wayne, Pa.

[21] Appl. No.: 776,453

[22] Filed: Mar. 10, 1977

[51] Int. Cl.² .................. C25B 3/00; C07C 51/08; C07C 63/26; C07C 63/28
[52] U.S. Cl. ............................. 204/180 P; 204/72; 204/263; 260/515 P
[58] Field of Search ............. 204/72 WS, 59 R, 72, 204/78, 180 R; 260/515 P

[56] References Cited

U.S. PATENT DOCUMENTS

| | | | |
|---|---|---|---|
| 2,770,588 | 11/1956 | Okada et al. | 204/72 |
| 3,086,928 | 4/1963 | Schulz | 204/72 |
| 3,113,964 | 12/1963 | Farkas et al. | 260/515 P |
| 3,393,220 | 7/1968 | Winnick et al. | 260/515 P X |
| 3,411,998 | 11/1968 | Wallman et al. | 204/98 |
| 3,781,343 | 12/1973 | Norton | 260/515 P |
| 3,849,243 | 11/1974 | Grot | 204/296 X |
| 3,968,017 | 7/1976 | Canata et al. | 204/18 P |
| 3,968,017 | 7/1976 | Canata et al. | 204/180 P |

FOREIGN PATENT DOCUMENTS 756,854  9/1956  United Kingdom ............. 204/72

OTHER PUBLICATIONS

Basic Principles Organic Chemistry by Roberts et al., p. 558, pub. by Benjamin, New York 1965.

Primary Examiner—F.C. Edmundson
Attorney, Agent, or Firm—J. Edward Hess; Donald R. Johnson; Paul Lipsitz

[57] ABSTRACT

A process for the preparation of terephthalic acid which comprises electrolyzing disodium terephthalate in the anode compartment of an electrolytic cell whereby terephthalic acid product is precipitated and subsequently separated. In a preferred embodiment the disodium terephthalate is obtained by the aqueous hydrolysis of terephthalonitrile in the presence of a stoichiometric excess of sodium hydroxide.

9 Claims, 2 Drawing Figures

TEREPHTHALIC ACID PROCESS

It is known in the art to hydrolyze terephthalonitrile in aqueous solution with or without catalysts to obtain terephthalic acid. In non-catalytic hydrolysis systems equilibrium reactions occur which cause nitrogen-containing intermediates to contaminate the terephthalic acid product. It therefore becomes extremely difficult to obtain the high purity terephthalic acid product needed for use as a polymer intermediate. Where alkaline catalysts (e.g. NaOH) are used for the nitrile hydrolysis, the product obtained will be an aqueous solution of the disodium salt of terephthalic acid and isolation of the free acid in pure form from such a solution is also difficult and expensive.

It is also known in the art to convert alkali metal carboxylic acid salts to free acid by electrolysis. More specifically, an alkali citrate is subjected to electrolysis to give the free acid (see for example U.S. Pat. Nos. 3,086,928 and 3,968,017). However, if pure citric acid is desired, then the alkali metal dihydrogen citrate is the starting material (U.S. Pat. No. 3,086,928). Where a di or tri-alkali metal salt is electrodialyzed as in U.S. Pat. No. 3,968,017 the product of the electrolysis is a mixture of salts and to obtain pure acid requires additional techniques to separate the unwanted salts.

It has now been found, unexpectedly, that free terephthalic acid of relatively high purity can be obtained by electrolysis of the di-alkali metal salt of terephthalic acid. It would have been expected that electrolysis of the di-salt would effect precipitation in the aqueous electrolysis medium of a mixture of the mono-salt and free acid. Surprisingly, however, the only product of the electroysis process is the free acid which precipitates from the aqueous medium and is easily filtered off.

In another embodiment of the invention terephthalonitrile is hydrolyzed in the presence of sodium hydroxide, the ammonia formed during the hydrolysis is removed and the disodium terephthalate solution subjected to electrolysis as set forth above.

The overall electrochemical reaction requires two Faradays to produce one mole of terephthalic acid product (TPA) and two moles of sodium hydroxide. The overall reaction may be shown as follows:

$$2Na_2TPA_{(anolyte)} + 6H_2O \rightarrow 2TPA_{(anolyte)} + O_{2(anode)} + 2H_{2(cathode)} + 4NaOH_{(cathode)}$$

In order to further illustrate and describe the process of the invention reference is made to the following drawings.

Figure 1:
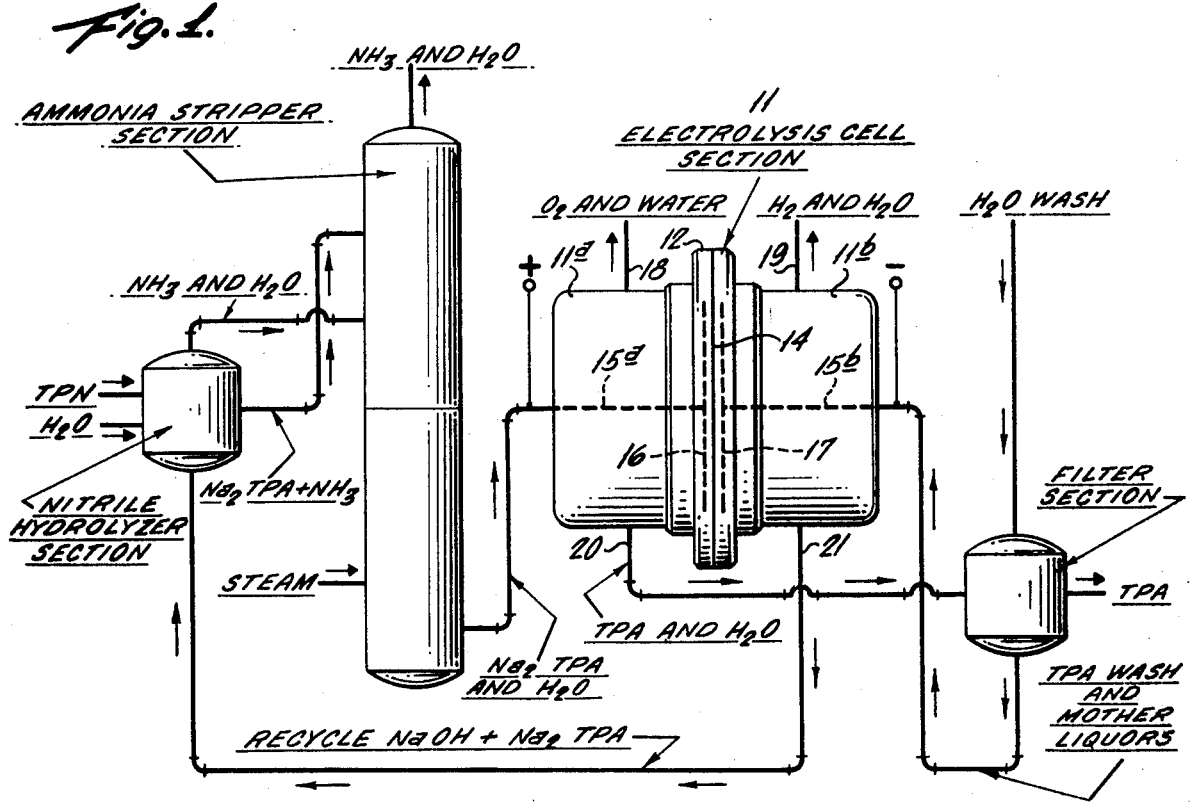
FIG. 1 is an overall view of the process wherein terephthalonitrile is hydrolyzed and the disodium salt of terephthalic acid electrolyzed.

Referring now to FIG. 1, it is seen that terephthalonitrile (TPN) and water are fed to the hydrolyzer section where hydrolysis occurs and ammonia and the disodium salt of terephthalic acid ($Na_2TPA$) are formed. The ammonia and water are removed from the hydrolysate, preferably by means of a steam stripping section as shown and the aqueous solution of $Na_2TPA$ passed into the anode section of an electrolysis cell where insoluble terephthalic acid (TPA) is generated. The TPA-water slurry is then processed in a filter section and the filtered, solid TPA washed and taken off as product, which if desired may be further purified by a recrystallization step to improve purity and/or give a more desirable particle size product. It will be noted that an aqueous solution of NaOH and $Na_2TPA$ from the cathode section of the electrolysis cell is recycled to the hydrolyzer section where it acts as the catalyst and reactant for the system. Also the TPA wash and mother liquors may be recycled to the cathode section of the electrolysis cell.

Figure 2:
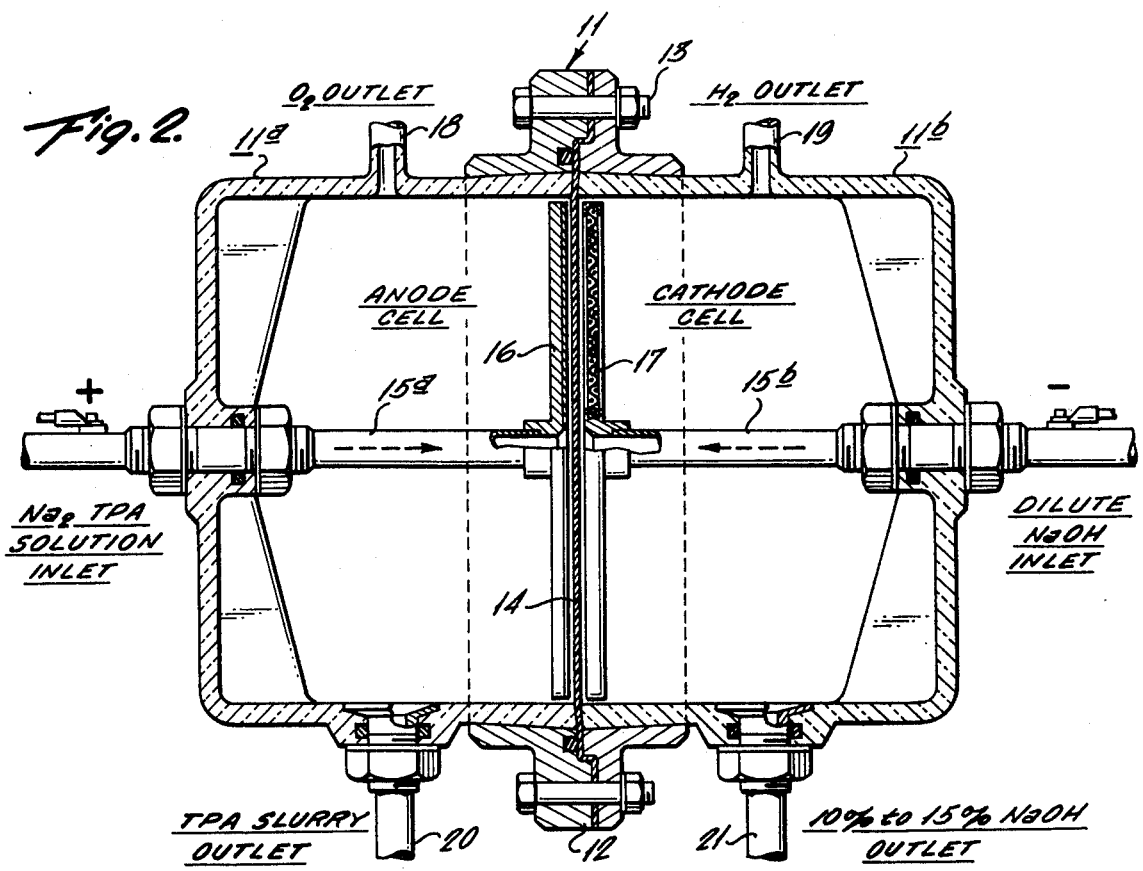
FIG. 2 is a detailed view of the electrolytic cell.

FIG. 2 illustrates the electrolysis apparatus in more detail. The electrolysis cell, shown generally as 11, is constructed of two cell sections of glass or other appropriate material 11a and 11b joined together at a flanged area 12 by a bolt 13 and separated by a membrane 14. The membrane will be cation selective to the passage of metal ions (e.g. $Na^+$), but not anions (e.g. $OH^-$). A preferred membrane is a perfluorosulfonic acid resin which is exemplified by the free sulfonic acid form of a perfluorocarbon sulfonyl fluoride copolymer; e.g., a copolymer of a perfluorinated alpha olefin (e.g. TFE) with a sulfonyl fluoride perfluoro vinyl ether. These copolymers and their membranes are known as NAFION ® membranes are made by E. I. duPont deNemours and Co., Inc., and are the subject of U.S. Pat. No. 3,282,875 which is hereby incorporated by reference.

Reference is also made to the DuPont magazine "Innovation" Volume 4, No. 3, Spring 1973 which discusses the chemistry of NAFION ® membranes and their use in electrolytic cells for plating and chlorine production at pages 11 and 12. Similar perfluorocarboxylic acid membranes which are also useful in the process of this invention are disclosed by Maomi Seko in an article appearing in Ind. Eng. Chem., Prod. Res. Dev. Vol 15, No. 4, 1976, pages 286–292.

Inputs for $Na_2TPA$ solution to the anode cell and dilute NaOH solution to the cathode cell will be by means of inert piping material 15a and 15b which are connected to a power supply to supply the appropriate voltage across the cell and which terminate respectively at an anode (16) and cathode 17. The cathode 17 will preferably be a stainless steel wire mesh positioned a short distance (about ⅛ inch) away from the membrane surface. The anode 16 is electroplatinized titanium, columbium or other suitably inert metal. Electroplated platinum anodes are preferred and flame deposited metal anodes should be be avoided as they rapidly become fouled and must be repeatedly cleaned either by washing with caustic or by reversing polarity in situ. At the top of the anode cell is an exit 18 for gaseous oxygen formed in the anode cell section and an exit 19 is positioned at the top of the cathode compartment for removal of hydrogen. An aqueous slurry of TPA is taken preferably by a gravity overflow system through the outlet 20 at the bottom of the anode compartment and a dilute NaOH solution is removed from outlet 21 at the bottom of the cathode cell.

In carrying out the nitrile hydrolysis the terephthalonitrile is mixed with water or dry fed into the hydrolysis section wherein a stoichiometric excess of sodium hydroxide (i.e. more than 2 moles of NaOH per mole of terephthalonitrile) hydrolyzes the nitrile into the disodium salt and ammonia:

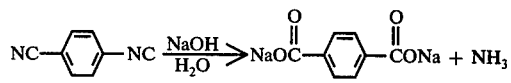

The much stronger base (NaOH) as well as the high ionic strength of the hydrolyzate effectively combine to diminish the concentration of $NH_3$ in the liquid phase and drive the $NH_3$ into the vapor phase. A suitably designed ammonia-water venting system tied to the vapor space of the hydrolysis reactor removes a stream of ammonia and steam which serves as an additional thermodynamic driving force for hydrolysis of TPN to 100% $Na_2TPA$. The hydrolysis conditions are an economic tradeoff between residence time and hydrolysis temperature although preferred conditions are between about 100° and about 250° C with a residence time of about 3 hours down to about 10 minutes with slightly more than 1 to about 3 equivalents respectively of NaOH per equivalent of nitrile functionality to be hydrolyzed. The hydrolysis section may consist of one or more stages to favorably shift hydrolysis equilibria and to prevent back-mixing.

The effluent from the hydrolyzer is at a temperature of from about 150° to about 250° C and comprises a solution of $Na_2TPA$ with excess NaOH and some dissolved free ammonia. Depending upon the exact hydrolytic conditions employed and the $Na_2TPA$ concentration in the hydrolyzate a variety of process options are available.

In one such option the effluent from the nitrile hydrolysis reactor might be adiabatically flash cooled to 80° C and stripped of residual ammonia to precipitate crystals of disodium terephthalate. In a preferred system, a continuous centrifuge removes the crystalline $Na_2TPA$ from the mother liquor which is recycled to the hydrolysis reactor. The crystalline $Na_2TPA$ is dissolved directly from the centrifuge to prepare a solution of $Na_2TPA$ of proper concentration and purity for efficient operation of the electrolysis cell.

The electrolysis cell converts the solution of sodium terephthalate (however derived by earlier processing) to a slurry of terephthalic acid in $Na_2TPA$ solution at the anode of the cell. The released sodium ions pass through the cation selective membrane to the cathode compartment under the applied voltage force. In the cathode compartment, there is formed a solution of sodium hydroxide with generation of hydrogen gas. The net reactions are:

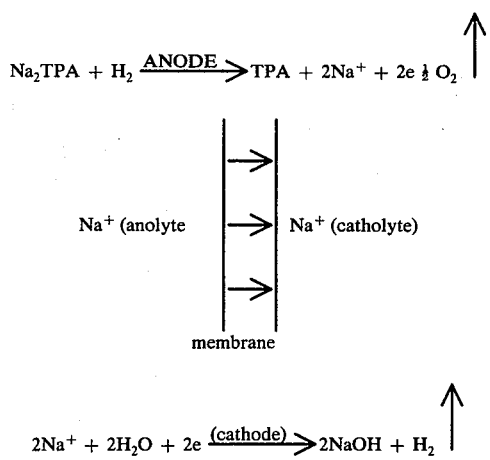

The electrolysis cell will be operated at atmospheric pressure and at a temperature of from about 60° to about 120° C, preferably at about 80° to about 95° C. The concentration of $Na_2TPA$ in the anode cell will be from about 0.1 to about 0.7 moles per liter with 0.6 to 0.7 moles per liter preferred. Current density will vary from about 100 to about 500 amps per square foot (ASF) (400 to 450 ASF preferred) at a voltage of from about 5 to about 12 volts, although voltage will generally be held below about 6.5 volts in order to render the process economical. Conversion of the $Na_2TPA$ to TPA will generally be between about 40 and 90%, but will preferably be at 60 to 70% in the interests of overall efficiency.

It will be understood that the degree of conversion of $Na_2TPA$ within the electrolysis cell will be controlled by the economic balance of power cost vs. plant investment (number and size of electroytic cells).

A unique aspect of this process is the continuous recycle of a high load (0.1–0.7 moles/liter) of $Na_2TPA$ through the anolyte compartment to maintain a high conductance of the anolyte whereby precipitation of terephthalic acid occurs without monosodium hydrogen terephthalate (NaHTPA). If NaHTPA were a product, the process would require further chemical treatment, or very high conversion per pass per cell and a much less efficient and higher cost process would result. It is the unexpected absence of NaHTPA which enables the process of the invention to be very suitable for commercialization.

As indicated, high conductance of the $Na_2TPA$ through the anolyte compartment is desirable. It has been observed that when the electrolysis is started with the desired high concentration of $Na_2TPA$ anolyte, the conductance is initially quite low and builds up to an efficient value only after a continue period of operation. However, a high initial conductance can be achieved if the initial $Na_2TPA$ anolyte solution is of lower concentration, usually about 25% of the desired operating concentration (e.g. about 0.025 to about 0.2 moles per liter). Thus, it is desirable in the interest of an efficient process to start the electrolysis with the lower concentration $Na_2TPA$ and during operation at the desired current level, switch to the higher concentration anolyte. This is readily done by pumping out the dilute solution while simultaneously pumping in the higher concentration replacement solution.

The effluent from the anode compartment, which represents a 30–80% conversion to terephthalic acid, and (on a continuous basis this is a 2.33 moles to - 0.25 moles $Na_2TPA$ recycle per mole TPA produced. This effluent is processed by filtration or centrifugation to remove the TPA. The mother liquor ($Na_2TPA/H_2O$) can be recycled to the anolyte feed, to the cathode compartment to dilute the NaOH solution, or pumped to the primary nitrile hydrolyzer to further increase its ionic strength and promote the rate of hydrodysis.

The crude TPA is washed or digested with water to remove the occluded salts, dried and packaged. The final wash is combined with the NaOH catholyte solution and recycled to the hydrolysis reactor.

In order to more fully illustrate the invention, the following examples are given.

EXAMPLE 1

An electrolysis cell apparatus of 3.2 square inches active area was utilized as shown in FIG. 2 wherein the anolyte and catholyte solutions were separated by a perfluorinated vinyl ether sulfonic acid copolymer type membrane (NAFION ® 425 membrane made by E. I. du Pont de Nemours and Co., Inc.). The cathode compartment recirculated dilute sodium hydroxide catholyte which was diluted with fresh water to maintain a 10-15% NaOH concentration. The hydrogen was vented to a gas line in a hood. Three liters of a solution of disodium terephthalate (0.33 moles/liter $Na_2TPA$) was recirculated at 40° C through the anode compartment of the apparatus. Electrolysis was started by applying 4 volts for approximately two minutes. During this time $O_2$ was evolved on the total length of the anode tube and on the anode screen itself. The cell initially evolved $O_2$ only on the anode surface adjacent to the membrane and after a short time the formation of white TPA crystals began. The following table indicates the various parameters and the results obtained.

| Time | Temp °C | Current, Voltage Applied & Observations |
| --- | --- | --- |
| 0 time | 42° | 2 amps 4 volts - cloudy solution - ppt forming - rapid $O_2$ & $H_2$ gas generation |
| 5 min. | 42° | 3.1 amps 6 volts -flocculent TPA formation |
| 15 min. | 43° | 3.3 amps |
| 25 min. | 43° | 3.5 amps |
| 35 min. | 44° | 3.6 amps |
| 50 min. | 45° | 3.7 amps |
| 80 min. | 45° | 3.7 amps - a tremendous amount of TPA suspended TPA |
| 110 min. | 43° | 3.2 amps - starting to filter TPA & recycling filtrate |
| 140 min. | 46° | 2.9 amps - recycling of filtrate |
| 145 min. | 46° | 2.4 amps - replaced recycling TPA & salt solution with only the $Na_2TPA$ salt solution free of TPA |
| 155 min. | 45° | 3.5 amps 10 volts |
| 175 min. | 45° | 2.6 amps 10 volts |

The total amount of solid TPA produced in the anode compartment and collected in the receiver was washed, dried at 130° and on analysis gave the following results:
  Terephthalic acid containing 0.22% Na
  Eq. wt. 86g/eq (theory 83)
  Yield 27.2g (0.16 moles)
  Conversion = 16%
  A small amount of TPA crystals formed a froth with the evolving oxygen gas bubbles and rose into the condenser tube on top of the anode compartment. Intermittently, the TPA in the condenser was washed into a beaker and collected. After completion of the experiment this sample was washed, dried and analyzed to give the following data:
  TPA-containing less than 50 ppm Na
  Eq. wt. = 82
  Yield 1.6g
  Thus, the total yield of TPA was 28.8g. representing a conversion of about 17%.

EXAMPLE 2

The apparatus used was a two compartment cell made by Ionics, Inc., Watertown, Mass. and known in the field under the trademark "Stack-Pak". The cell active area was 51.5 square meters and the membrane was of Dupont NAFION material. The anode was platinum electroplated on titanium and the cathode was stainless steel.

At the beginning of each run, a 0.6 molar solution of 126 g/l of $Na_2TPA$ was placed in the anolyte reservoir while a 5% by weight caustic of a known normality was placed in the catholyte reservoir. Both solutions were heated to as high a temperature as possible (generally about 75° C) to take advantage of increasing conductance with temperature. The solutions were circulated respectively through the anolyte and catholyte compartments while direct current was passed through the cell from a constant current rectifier. A small basket centrifuge was placed in the anolyte recirculation line to remove the free TPA product as formed. As the electrolysis proceeded the voltage required to maintain the desired current level was monitored, and the samples of the base solution were titrated to determine the extent of conversion and current efficiency. No attempt was made to monitor the oxygen and hydrogen releases.

All runs in this series were made at a current density of about 120 ASF. There was no severe anode fouling as was found with a flame deposited platinum anode in a similar previous experiment. Anodes which were partially fouled with TAP were completely cleaned by reversal of cell voltage.

The following table indicates the cell performance:

| Cell Performance | | | | |
| --- | --- | --- | --- | --- |
| Amperage | Voltage | Current Density (ASF) | ASF/V | Time,Hours |
| 24 | 6.2 | 224 | 36 | 0.5 |
| 32 | 6.2 | 299 | 48 | |
| 36 | 6.6 | 336 | 51 | |
| 44 | 7.2 | 411 | 57 | |
| 45 | 7.2 | 421 | 58 | |
| 36 | 6.2 | 336 | 54 | |
| 26 | 5.4 | 243 | 44 | |
| 47 | 7.2 | 439 | 61 | |
| 49 | 7.0 | 458 | 65 | 2.5 |

From these above runs it is clear that some "conditioning" of either the cell or charge solution occurs during the first 30 minutes of operation.
It is possible to operate at high current densities in the region of 400 ASF at reasonable cell voltages, i.e., about 6 - 7 volts. Also it is clear that cell performance increases with increasing conversion.

The solids produced in the above series of runs were analyzed with and without hot water washing. The sodium levels for two typical samples are shown below:

| Na Contamination of Product TPA | |
| --- | --- |
|  | PPM Na |
| No Washing | 28000 |
| Hot (100° C) $H_2O$ Washing | 40 |

EXAMPLE 3

When Example 2 was repeated, but at 63 g. $Na_2TPA$/liter (0.3 molar), using an initial voltage of 5 volts, free TPA began precipitating out after a few minutes. The voltage was then increased to 6.2 v. and the amperage increased to 45 amps (about 420 ASF). Cell operation was continued for about one hour with the constant production of TPA.

With a similar run at 95 g. $Na_2TPA$ per liter the same cell performance as that found above was obtained. In both the 63g. and 95 g. $Na_2TPA$ per liter concentration runs, there was no fouling of electrodes and constant production of TPA.

EXAMPLE 4

Using the cell of Example 1 and operating at 6-° C, TPA was produced continuously for two hours at a current density of 500 ASF using an applied voltage of 6.2 volts. In starting this run a dilute solution of $Na_2TPA$ (32 g/l) was used initially and then as electrolysis was proceeding (at 500 ASF current density which was reached immediately) a replacement of a higher concentration solution (126 g/l) was used to replace the initial solution. This procedure makes it possible to quickly achieve high current densities which is desirable for efficient operation.

EXAMPLE 5

Disodium terephthalate was prepared by hydrolysis of terephthalonitrile in the following manner. Terephthalonitrile (128 g, 1.0 mol) was added over a period of ten minutes to a boiling solution of 2.05 moles Sodium hydroxide in 500 ml. of water. Within 30 sec. there started a copious release of ammonia. The slurry was boiled for five hours during which time the slurry became a momogenous solution. Evaporation of the 500 ml of reaction volume to 100 ml. and cooling of the solution effected precipitation from solution of disodium terephthalate (185 g, 0.88 mol) containing less than 100 ppm of residual nitrogen content.

The disodium terephthalate from the above hydrolysis provides a useful source of $Na_2TPA$ for conversion to terephthalic acid as described in the above examples.

The invention claimed is:

1. A process for the preparation of terephthalic acid which comprises electrolyzing in the anode compartment of an electrolysis cell wherein said anode compartment is separated from the cathode compartment by a cation selective membrane, an aqueous solution of sodium terephthalate at a molar concentration of from about 0.1 to about 0.7 to form an aqueous suspension of terephthalic acid and separating said terephthalic acid product, said electrolysis being conducted at a temperature of from about 60° to about 120° C, a current density of from about 100 to about 500 amps per square foot, and at a voltage of from about 5 to about 12 volts.

2. The process of claim 1 wherein the anode of said cell is electroplated platinum.

3. The process of claim 2 wherein the cell is operated at a temperature between about 80° and about 95° C, a current density of from about 400 to about 450 ASF and a voltage of about 5 to about 6.5 volts.

4. The process of claim 3 where the cation selective membrane is a perfluorosulfonic acid resin.

5. The process of claim 4 where the concentration of sodium terephthalate is initially from about 0.025 to about 0.2 moles per liter and is increased during electrolysis to a concentration of from about 0.6 to about 0.7 moles per liter.

6. A process for the preparation of terephthalic acid which comprises hydrolyzing terephthalonitrile in an aqueous medium containing a stoichiometric excess of sodium hydroxide at a temperature of between about 100° and about 250° C, removing ammonia generated by the hydrolysis from the aqueous medium, subjecting an aqueous solution containing from about 0.1 to about 0.7 molar per liter of sodium terephthalate obtained by said hydrolysis to electrolysis in the anode compartment of an electrolysis cell wherein said anode compartment is separated from the cathode compartment by a cation selective membrane to form an aqueous suspension of terephthalic acid and separating said terephthalic acid product, said electrolysis being conducted at a temperature of from about 60° to about 120° C, a current density of from about 100 to about 500 amps per square foot, and at a voltage of from about 5 to about 12 volts.

7. The process of claim 6 where the cation selective membrane is a perfluorinated sulfonic or carboxylic acid resin and the anode is electroplated platinum.

8. The process of claim 7 where the cell is operated at a temperature between about 80° and about 95° C, a current density of from about 400 to about 450 ASF, voltage of from about 5 to about 6.5 volts and the concentration of aqueous sodium terephthalate in the anode compartment is from about 0.6 to about 0.7 moles per liter.

9. The process of claim 7 wherein the concentration of sodium terephthalate in the anode compartment is initially about 25% of the desired operating concentration.

* * * * *